United States Patent
Laronda et al.

(10) Patent No.: US 10,479,980 B2
(45) Date of Patent: Nov. 19, 2019

(54) ARTIFICIAL OVARY

(71) Applicant: Northwestern University, Evanston, IL (US)

(72) Inventors: Monica M. Laronda, Chicago, IL (US); Alexandra L. Rutz, Chicago, IL (US); Ramille N. Shah, Hinsdale, IL (US); Teresa K. Woodruff, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 162 days.

(21) Appl. No.: 15/545,175

(22) PCT Filed: Jan. 28, 2016

(86) PCT No.: PCT/US2016/015398
§ 371 (c)(1),
(2) Date: Jul. 20, 2017

(87) PCT Pub. No.: WO2016/123362
PCT Pub. Date: Aug. 4, 2016

(65) Prior Publication Data
US 2017/0369851 A1  Dec. 28, 2017

Related U.S. Application Data

(60) Provisional application No. 62/109,754, filed on Jan. 30, 2015.

(51) Int. Cl.
| | | |
|---|---|---|
| *C12N 5/071* | (2010.01) | |
| *C12N 5/075* | (2010.01) | |
| *A61K 35/54* | (2015.01) | |
| *B33Y 80/00* | (2015.01) | |
| *B33Y 70/00* | (2015.01) | |
| *B29C 64/106* | (2017.01) | |
| *B29L 31/00* | (2006.01) | |

(52) U.S. Cl.
CPC ............ *C12N 5/0697* (2013.01); *A61K 35/54* (2013.01); *B29C 64/106* (2017.08); *B33Y 70/00* (2014.12); *B33Y 80/00* (2014.12); *C12N 5/0609* (2013.01); *C12N 5/0682* (2013.01); *B29K 2089/00* (2013.01); *B29L 2031/7532* (2013.01); *C12N 2502/04* (2013.01); *C12N 2502/243* (2013.01); *C12N 2513/00* (2013.01); *C12N 2533/54* (2013.01); *C12N 2533/90* (2013.01); *C12N 2537/10* (2013.01)

(58) Field of Classification Search
None
See application file for complete search history.

(56) References Cited

U.S. PATENT DOCUMENTS

| | | | |
|---|---|---|---|
| 7,049,057 B2 | 5/2006 | Atala et al. | |
| 8,361,503 B2 | 1/2013 | Badylak et al. | |
| 8,535,719 B2 | 9/2013 | Badylak et al. | |
| 8,691,276 B2 | 4/2014 | Badylak et al. | |
| 9,314,340 B2 | 4/2016 | Badylak et al. | |
| 2008/0268019 A1 | 10/2008 | Badylak et al. | |
| 2010/0256777 A1 | 10/2010 | Datta et al. | |
| 2010/0267143 A1 | 10/2010 | Park et al. | |
| 2011/0212481 A1 | 9/2011 | Morgan et al. | |
| 2014/0023723 A1 | 1/2014 | Leach et al. | |
| 2014/0113373 A1 | 4/2014 | Chien et al. | |
| 2014/0335144 A1 | 11/2014 | Ward et al. | |
| 2015/0231302 A1 | 8/2015 | Duvall et al. | |
| 2017/0081534 A1 | 3/2017 | Shah et al. | |
| 2017/0283771 A1* | 10/2017 | Telfer | C12N 5/0682 |

FOREIGN PATENT DOCUMENTS

| | | |
|---|---|---|
| EP | 2211925 | 8/2010 |
| WO | WO2007011644 | 1/2007 |
| WO | WO2007087402 | 8/2007 |
| WO | WO2010030964 | 3/2010 |
| WO | WO2011005974 | 1/2011 |
| WO | WO2014039429 | 3/2014 |

OTHER PUBLICATIONS

International Search Report and Written Opinion mailed in PCT/US2017/062218, Feb. 9, 2018.
Hornick et al., Multiple follicle culture supports primary follicle growth through paracrine-acting signals, Reproduction 145, Oct. 29, 2012, pp. 19-32.
Jeruss et al., Preservation of Fertility in Patients with Cancer, N Engl J Med 360, Feb. 26, 2009, pp. 902-911.
Rutz et al., a Multimaterial Bioink Method for 3D Printing Tunable, Cell-Compatible Hydrogels, Adv. Mater. 27, Jan. 16, 2015, pp. 1607-1614.
Woodruff et al., The Role of the Extracellular Matrix in Ovarian Follicle Development, Reproductive Sciences, vol. 14, No. 8S, Dec. 2007, pp. 6-10.
Woodruff et al., A new hypothesis regarding ovarian follicle development: ovarian rigidity as a regulator of selection and health, J Assist Reprod Genet 28, Sep. 25, 2010, pp. 3-6.
Xu et al., Tissue-Engineered Follicles Produce Live, Fertile Offspring, Tissue Engineering, vol. 12, No. 10, 2006, pp. 2739-2746.
Hornick et al., Isolated primate primordial follicles require a rigid physical environment to survive and grow in vitro, Human Reproduction, vol. 27, No. 6, Mar. 28, 2012, pp. 1801-1810.

(Continued)

*Primary Examiner* — Allison M Fox
(74) *Attorney, Agent, or Firm* — Bell & Manning, LLC

(57) ABSTRACT

Artificial ovaries comprising porous three-dimensional scaffolds are provided. Also provided are ink compositions and methods for printing the scaffolds. The artificial ovaries have spatial arrangements and cellular compositions that allow them to mimic native ovarian tissue. As such, they can be cultured or transplanted to support female endocrine function and/or the development of oocytes and/or eggs.

35 Claims, 8 Drawing Sheets

(56) References Cited

OTHER PUBLICATIONS

West et al., Physical properties of alginate hydrogels and their effects on in vitro follicle development, Biomaterials 28, 2007, pp. 4439-4448.
Shikanov et al., A Method for Ovarian Follicle Encapsulation and Culture in a Proteolytically Degradable 3 Dimensional System, Journal of Visualized Experiments, Issue 49, Mar. 15, 2011, pp. 1-9.
Vanacker et al., Transplantation of an alginateematrigel matrix containing isolated ovarian cells: First step in developing a biodegradable scaffold to transplant isolated preantral follicles and ovarian cells, Biomaterials 33, May 31, 2012, pp. 6079-6085.
S. Hollister, Porous scaffold design for tissue engineering, nature materials, vol. 4, Jul. 2005, pp. 518-524.
Murphy et al., 3D bioprinting of tissues and organs, Nature Biotechnology, vol. 32, No. 8, Aug. 5, 2014, pp. 773-785.
Xu et al., A three-dimensional in vitro ovarian cancer coculture model using a high-throughput cell patterning platform, Biotechnol. J., 6, 2011, pp. 204-212.
Luyckx et al., First step in developing a 3D biodegradable fibrin scaffold for an artificial ovary, Journal of Ovarian Research, 6, 2013.
Researchers build 'artificial ovary' to develop oocytes into mature human eggs, Brown University Press Release, Sep. 14, 2010.
Woodruff et al., Bioengineering and the Ovarian Follicle, Chapter 6 from Oncofertility Fertility Preservation for Cancer Survivors, 2007, pp. 75-82.
Kniazeva et al., Primordial Follicle Transplantation within Designer Biomaterial Grafts Produce Live Births in a Mouse Infertility Model, Scientific Reports 5:17709, Dec. 3, 2015.
Krotz et al., In vitro maturation of oocytes via the pre-fabricated self-assembled artificial human ovary, J Assist Reprod Genet, 27, Aug. 25, 2010, pp. 743-750.
International Search Report and Written Opinion mailed in PCT/US2016/015398, dated Apr. 22, 2016.
Laronda et al., Engineered Endocrine Organ Transplant Utilizing a Decellularized Ovary Scaffold, Endocrine Society's 96th Annual Meeting and Expo, Chicago, Jun. 21, 2014.
Xu et al., Secondary Follicle Growth and Oocyte Maturation by Culture in Alginate Hydrogel Following Cryopreservation of the Ovary or Individual Follicles, Biotechnology and Bioengineering, vol. 103, No. 2, Jun. 1, 2009, pp. 378-386.
Rutz et al., Bioengineering an Artificial Ovary with 3D Printing, Abstract for Poster Presentation at Society for Biomaterials 2015 Annual Meeting (Apr. 2015).
Laronda et al., Initiation of puberty in mice following decellularized ovary transplant, Biomaterials 50, May 2015, pp. 20-29.

\* cited by examiner

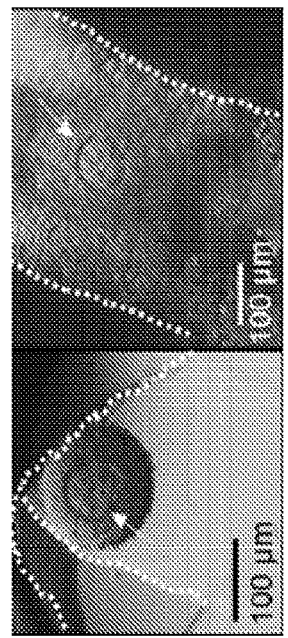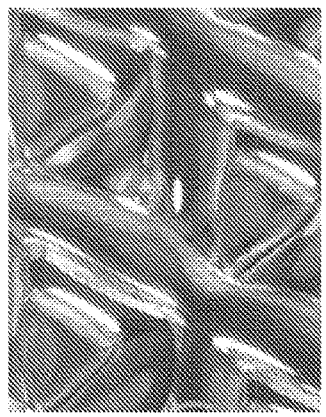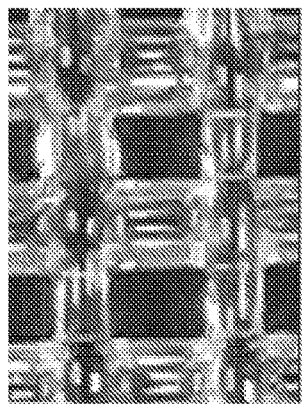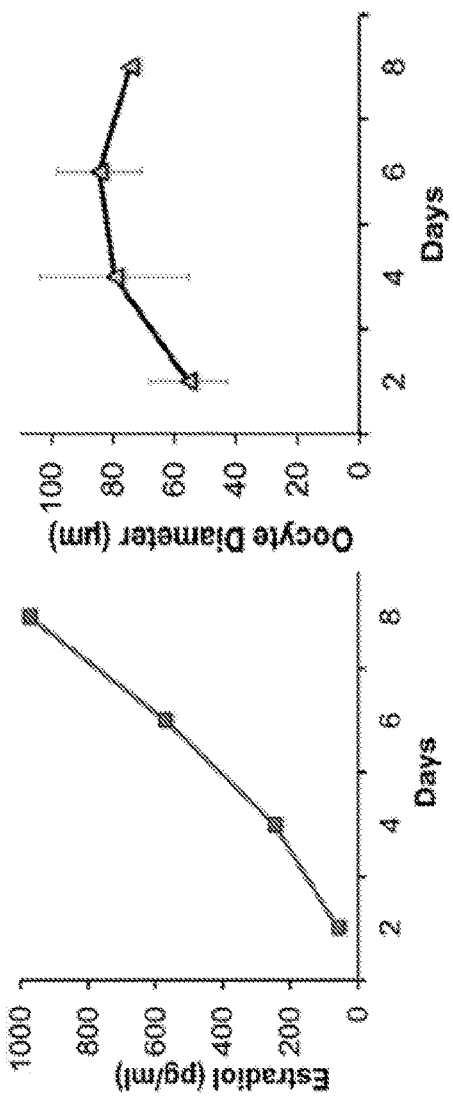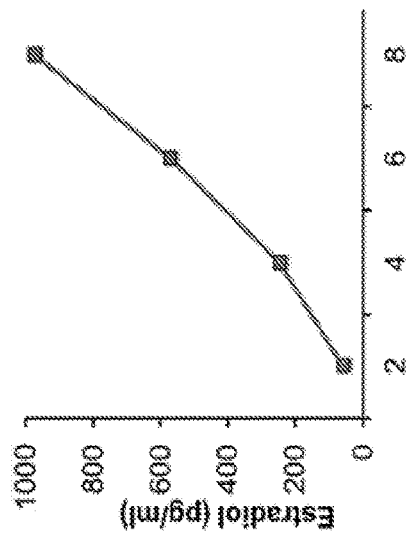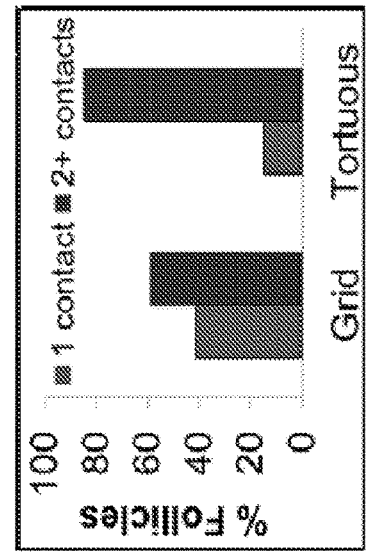
FIG. 1A  FIG. 1B  FIG. 1F  FIG. 1G  FIG. 1D  FIG. 1H  FIG. 1E

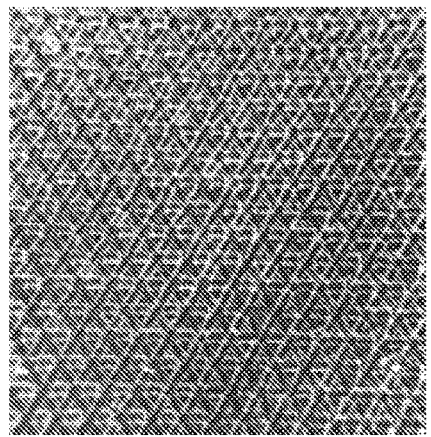
FIG. 2A
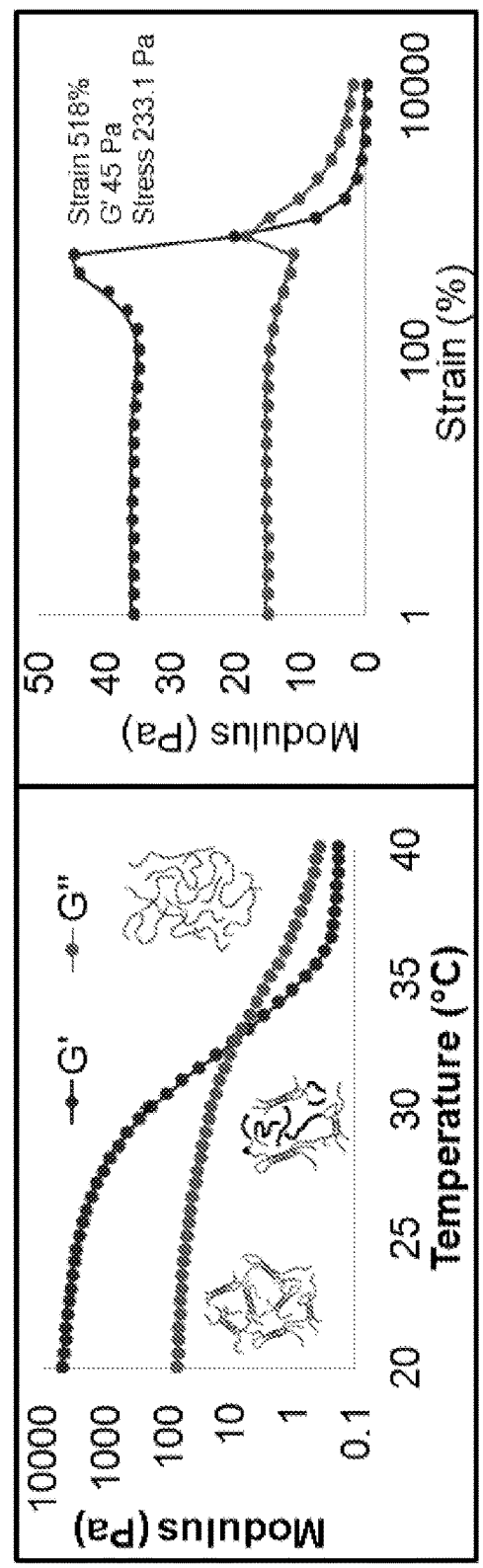
FIG. 2B
FIG. 2C

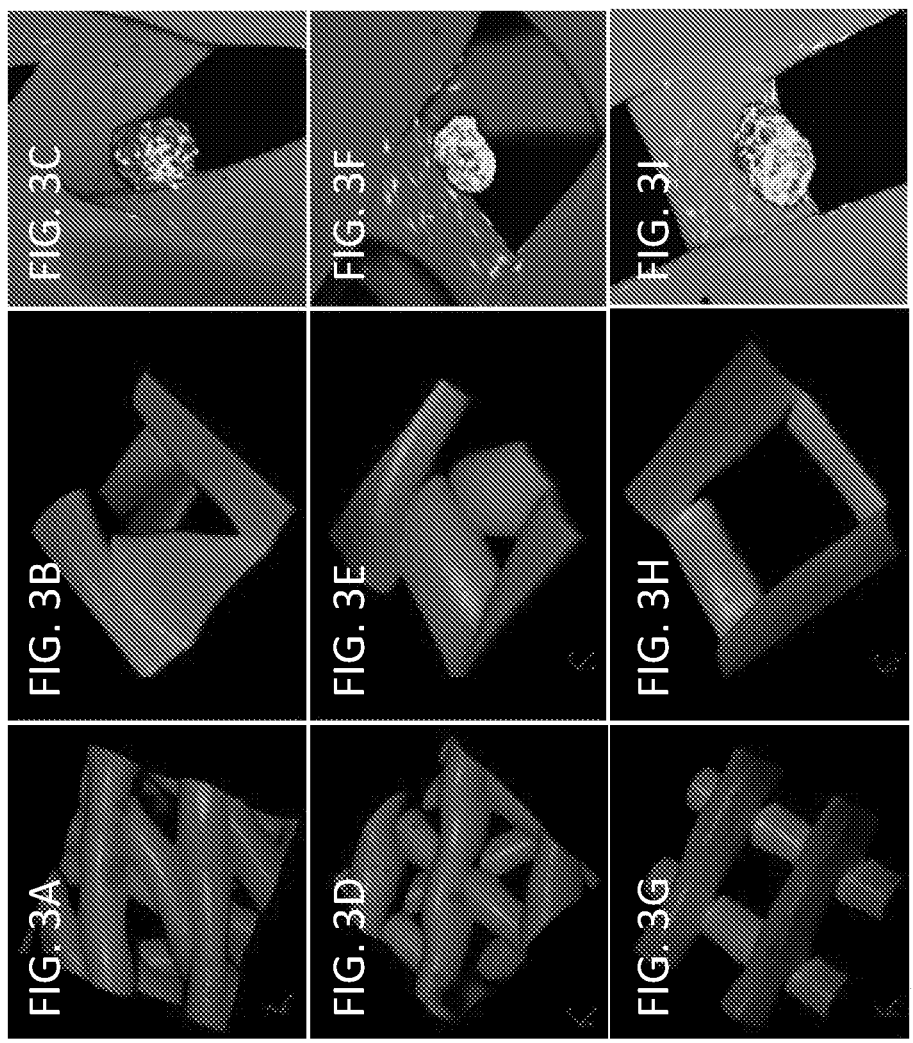

ARTIFICIAL OVARY

CROSS-REFERENCE TO RELATED APPLICATIONS

This application is a National Stage of International Application No. PCT/US2016/015398, that was filed on Jan. 28, 2016, the contents of which are incorporated herein by reference; which claims the benefit of U.S. Provisional Patent Application No. 62/109,754, that was filed on Jan. 30, 2015, the contents of which are incorporated herein by reference.

REFERENCE TO GOVERNMENT RIGHTS

This invention was made with government support under K01 DK099454 and HD079188 awarded by the National Institutes of Health. The government has certain rights in the invention.

BACKGROUND

Women suffer harsh consequences of gonadal toxicity and dysfunction that arise from chemotherapy and radiation therapies and developmental disorders. Treatment options are limited for resulting infertility, hormone insufficiency, and inability to go through puberty. The female ovary includes follicles, cell spheroids possessing the oocyte, and somatic cells responsible for hormone production and cycling. In humans, autotransplant of cryopreserved ovarian tissue has given patients short-term hormone cycling (<19 months) and live birth. (See, Jeruss J. N Engl J Med. 2009:360(9):902-11 and Ernst E. European Journal of Cancer. 2013; 49 (4):911-914.) Autotransplants, which are only available for patients suffering gonadotoxicity from cancer therapies, pose a risk of cancer and possess a short life span. (See, Bastings L. Hum Reprod Update. 2013; 19(5):483-506.)

Great advances in follicle culture and transplant, including live birth in mice, have been made with biomaterial strategies, most commonly hydrogel bead seeding or encapsulation. (See, Xu M. Tissue Engineering. 2006; 12(10): 2739-2746.) These strategies, however, do not permit advanced design to optimize transplant function of a sustaining follicle pool. For example, in follicle culture, when follicles are seeded on top of a scaffold, the follicles observe a two-dimensional surface. As a result, the three-dimensional structure of the follicle is not supported and the stromal cells, the cells that comprise most of the follicle, leave the oocyte. Once these stromal cells leave the oocyte, the oocyte dies and there is no longer cell function. Alternatively, the follicles can be injected into and encapsulated by a hydrogel bead. In hydrogel encapsulation, the stroma cell-follicle contacts are preserved. However, in hydrogel encapsulation, only very soft (low stiffness) hydrogels can be used, otherwise the follicle will not be able to grow. Because the stiffness of the hydrogel provides a biological cue, the hydrogel beads are unable to provide an optimal material for follicle development and have been unable to restore whole organ function with cyclical endocrine production and response.

SUMMARY

Artificial ovaries comprising three-dimensional scaffolds are provided. Also provided are ink compositions and methods for printing the scaffolds. The artificial ovaries can be used to ovulate an egg in vitro or in vivo and can be implanted in a subject to restore ovary function.

One embodiment of an artificial ovary comprises: a porous three-dimensional scaffold comprising a plurality of overlapping struts, the struts comprising a biocompatible polymer and defining a network of pores; and a plurality of ovarian follicles disposed inside the pores. This artificial ovary is capable of supporting at least one of: an ovarian endocrine function; or ovulation of one or more mature oocytes from one or more of the ovarian follicles, when the artificial ovary is cultured in vitro or implanted in a mammalian subject in vivo.

One embodiment of method of making an artificial ovary, the method comprises: extruding a composition comprising water and a biocompatible polymer through a nozzle to form a porous three-dimensional scaffold comprising a plurality of overlapping struts that form a network of open pores; and incorporating ovarian follicles into the pores. The resulting artificial ovary is capable of supporting at least one of: an ovarian endocrine function; or ovulation of one or more mature oocytes from one or more of the ovarian follicles, when the artificial ovary is cultured in vitro or implanted in a mammalian subject in vivo.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIG. 1A. Gelatin scaffold with a square grid-like pattern.

FIG. 1B. An embodiment of a gelatin scaffold with a tortuous pattern.

FIG. 1D. Graph of estradiol production by a follicle seeded scaffold over 8 days.

FIG. 1E. Graph of the percentage of follicles making 1 or 2+ contacts with struts in gelatin scaffolds with a square grid-like pattern and a more tortuous pattern.

FIG. 1F. Light image of an intact follicle in a tortuous scaffold after 6 days (struts dashed).

FIG. 1G. Light image of a dissociated follicle in a square grid scaffold after 6 days (struts dashed).

FIG. 1H. Graph showing the average oocyte diameter for follicles in a scaffold cultured over 8 days.

FIG. 2A. An image of a scaffold printed at an advancing angle of 60°.

FIG. 2B. The gelation profile of gelatin over 40 to 15° C.

FIG. 2C. shows the response of 30 ° C. gelatin to increasing strains.

FIG. 3A. 3D reconstruction of a confocal fluorescence image of stacked layers comprising struts printed at an advancing angle of 30°.

FIG. 3B. 3D reconstruction of a confocal fluorescence image of stacked layers comprising struts printed at an advancing angle of 60°.

FIG. 3C. 3D reconstruction of a confocal fluorescence image of stacked layers comprising struts printed at an advancing angle of 90°.

FIG. 3D. 3D reconstructions of the pores in the confocal fluorescence image of the stacked layers comprising struts printed at an advancing angle of 30°.

FIG. 3E. 3D reconstructions of the pores in the confocal fluorescence image of the stacked layers comprising struts printed at an advancing angle of 60°.

FIG. 3F. 3D reconstructions of the pores in the confocal fluorescence image of the stacked layers comprising struts printed at an advancing angle of 90°.

FIG. 3G. EGFP-expressing follicles seeded in a pore of the scaffold of FIG. 3A, after 2 days.

FIG. 3H. EGFP-expressing follicles seeded in a pore of the scaffold of FIG. 3B, after 2 days.

FIG. 3I. EGFP-expressing follicles seeded in a pore of the scaffold of FIG. 3C, after 2 days.

DETAILED DESCRIPTION

Figure 1C:
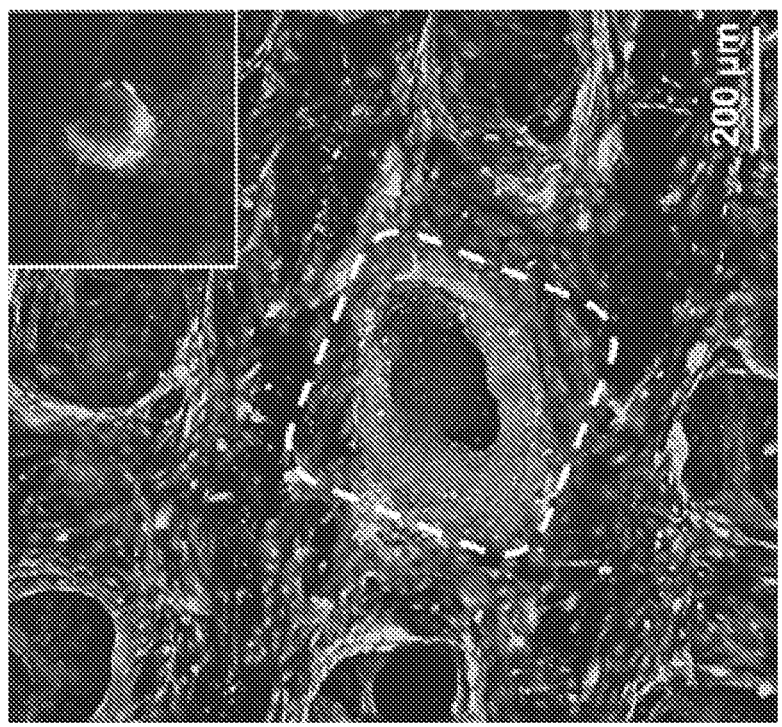
FIG. 1C. Fluorescence image of somatic cells coating the struts of a scaffold, follicle seeded in pore (circled), Live/dead stain; inset: somatic cells (light grey) surrounding follicle (white).

Artificial ovaries comprising porous three-dimensional scaffolds are provided. Also provided are ink compositions and methods for printing the scaffolds. The artificial ovaries have spatial arrangements and cellular compositions that allow them to mimic native ovarian tissue. As such, they can be cultured or transplanted to support female endocrine function and/or the development of oocytes and/or eggs. This makes the artificial ovaries useful in many applications including implants for restoring pubertal hormones in children, restoring fertility and/or providing endocrine support in women, creating an organ mimic with genome-specific cells for the investigation of different disease traits or response to pharmacological or chemical agents, providing an organ mimic as a basic science tool to investigate ovarian cell-cell and cell-material interactions, and/or to control follicle maturation and ovulation in vitro for in vitro fertilization (IVF) applications.

Some embodiments of the artificial ovaries provide an implantable, functional ovarian bioprosthesis—an engineered female gonad, comprised of biodegradable biomaterials (natural or synthetic) and ovarian cells, that achieves reproductive function and endocrine support in vivo that can replace a diseased, damaged or insufficiently functioning ovary of the recipient patient.

The artificial ovaries need not be capable of supporting a female endocrine function and/or the development of oocytes and/or eggs indefinitely. The period over which they need to perform these functions will depend on their intended application. However, for the purposes of this disclosure, an artificial ovary is considered to support female endocrine function and/or the development of oocytes and/or eggs if it performs these functions for at least 8 days, as illustrated by the examples, below. Although the period over which the artificial ovaries perform these functions can be substantially longer, including periods of one month or longer, 6 months or longer, and one year or longer.

The artificial ovaries comprise a porous three-dimensional scaffold that defines a network of open pores. The scaffolds are characterized by an open macroporosity that supports ovarian follicle function when follicles are seeded in the pores. In some embodiments of the artificial ovaries, the scaffolds are printed and, therefore, comprise a plurality of struts that define the network of open pores. The scaffolds are composed of one or more biocompatible polymers and, optionally, ovarian somatic cells are incorporated into or adhered onto the scaffold. In some embodiments, the ovarian somatic cells form a uniform cell coating on the scaffold. The ovarian somatic cells may include stroma cells, endothelial cells, ovarian hormone producing cells, pericytes, pericyte precursor cells (e.g., mesenchymal stem cells) and mixtures thereof. Ovarian follicles are seeded within the pores of the scaffold.

The ovarian somatic cells and follicles used to construct the artificial ovaries can be obtained from a subject into whom they are to be implanted, from a donor subject, or from differentiation induced pluripotent or embryonic stem cells. The subjects may be mammalian, including human.

The porous scaffolds can be formed from ink compositions using 3D printing techniques. In these techniques an aqueous ink composition comprising a biocompatible polymer is extruded through a nozzle to form the struts of the porous three-dimensional scaffold. Ovarian somatic cells can be incorporated into the struts of the scaffold by including them in the initial ink composition, or they can be seeded onto the scaffold post-printing. The use of 3D printing for the fabrication of the scaffolds is advantageous because it provides for regular geometric patterning of the sequential layers that make up the scaffold, which makes it possible to control and tailor the porosity, pore size, and pore interconnectivity of the scaffold. 3D printing also provides on-demand scaffold design, material selection, and cell placement within 3D scaffolds.

The porous scaffolds can be printed via multiple layer-by-layer extrusions of the ink composition through a nozzle, such as a print nozzle in the print head of a printer, such as a bioplotter (e.g., Envision TEC, GmbH), or through a capillary, the needle of a syringe, or the like. In one embodiment of a printing process, the ink composition is loaded into an ink cartridge of a 3D printer and extruded through the orifice in one or more print nozzles via pneumatic or mechanical pressure. The layer-by-layer extrusion technique can be repeated until a scaffold having the desired thickness and comprising the desired number of layers has been fabricated. The printing technique can form a stack of layers, wherein each layer is comprised of a plurality of struts and the struts in a given layer overlap (i.e., are layered on top of) the struts in the previously printed, underlying layer. Extrusion through the nozzle ensures that the struts will have a substantially uniform cross-section along their lengths. (In this context "substantially uniform" is used in recognition that the extrusion process is not perfect and may result in some cross-sectional non-uniformity based on the limitations of the printing equipment. Therefore, a printed strut having a cross-sectional diameter that varies by no more than ±30% along its length, is considered to have a substantially uniform cross-section along its length. This includes struts having a cross-sectional diameter that varies by no more than ±20%, no more than ±10%, or no more than ±5% along its length.)

The printed (i.e., extruded) struts (referred to as "fibers"), which form the scaffolds, can be printed in a regular, repeating pattern, can be printed in a random arrangement, or in some combination of both. In a regular arrangement of struts, the struts in a layer can be spaced apart and substantially aligned along their long axes. (In this context "substantially aligned" is used in recognition that the extrusion process is not perfect and may result in some minor non-uniformity in the alignment of the struts based on the limitations of the printing equipment. Therefore, neighboring struts separated by a spacing that varies by no more than ±30% along the lengths of the struts, are considered to be substantially aligned. This includes struts having a spacing that varies by no more than ±20%, no more than ±10% or no more than ±5% along their lengths.) If the struts are straight, this results in a layer comprising a series of substantially parallel struts. In such a regular arrangement of struts, the struts in adjacent layers may be extruded at angles ranging from 0° to 360° with respect to each other to form a regular grid pattern, as shown in FIGS. 3A-3C. For the purpose of this disclosure, the angle defined between a strut in one layer and a strut in an adjacent layer in a layered stack is referred to as the advancing angle. By way of illustration, an advancing angle of 90° can be used to form a regular square grid, as shown in FIG. 3C. Alternatively, the struts in different layers can be extruded at smaller advancing angles to provide a scaffold having a more tortuous pore arrangement, as shown in FIGS. 3A and 3B.

The pores in the scaffold are large enough that ovarian follicles can fit inside the pores and adhere to at least one—and preferably more than one (e.g., at least two; at least three; or at least 4)—strut. A higher number of strut contacts is desirable because ovarian follicles in the pores may have more favorable interactions between the ovarian somatic cells, such as ovarian stroma cells, and the follicles and, therefore, a higher survival rate when the artificial ovaries are cultured or implanted. The pores can be significantly larger than, or only slightly larger than, the follicles to be seeded within the scaffold. The optimal average pore size for a given scaffold will depend on the growth stage of the isolated follicles to be grown (i.e., mammalian (e.g., mouse or human) primordial, primary, secondary, and/or antral). By way of illustration only, in some embodiments of the artificial ovaries, the average pore size in the scaffold is in the range from about 35 μm to about 2 mm. This includes embodiments of the artificial ovaries in which the scaffold has an average pore size in the range from about 100 μm to about 1 mm and still further includes artificial ovaries in which the scaffold has an average pore size from about 100 μm to 500 μm. The pore size of the scaffold is based on the pore defined by the struts and does not take into account any in-filling by seeded cells or in-grown biological tissue. The size of a pore formed by two adjacent layers of struts can be determine by imaging/viewing the pore defined by the struts in two adjacent layers from above. If the pores are defined by adjacent layers comprising substantially aligned struts, the pore size will correspond to the spacing between the substantially aligned struts. If strut spacing in one of the layers defining a pore is larger than the strut spacing in the adjacent layer, the pore size corresponds to the larger spacing.

The number of follicles incorporated into the scaffolds can vary from 1, or just a few, to tens (e.g., 10-100); hundreds (e.g., 100-1000); thousands (1000-10,000); tens of thousands (10,000-100,000); or even greater.

Appropriate pore sizes and geometries can be attained by using struts having an appropriate spacing and advancing angles. In addition, the struts desirably have diameters that are at least as large as the diameter of the ovarian follicles to be seeded in the pores. For example, in some embodiments of the scaffolds the struts have diameters in the range from 10 μm to 1 mm with a regular intra-layer strut spacing in the range from 50 μm to 1 mm. (Unless otherwise specified, the endpoints in a recited range are including in that range.) This includes scaffolds in which the struts have diameters in the range from 100 μm to 400 μm and further includes scaffolds in which the struts have diameters in the range from 100 μm to 300 μm. Some embodiments of the scaffolds have a regular strut spacing within each layer in the range from 50 μm to 600 μm, including scaffolds having a regular intra-layer strut spacing in the range from 100 μm to 600 μm; from 400 μm to 600 μm; and from 300 μm to 500 μm.

In some embodiments, the scaffolds comprise stacked structures in which the struts in sequentially printed layers are substantially straight and aligned with advancing angles in the range from 20° to 80°. In some such embodiments the advancing angles are within the range from 25° to 75°; 25° to 65°; and 30° to 60°. However, a variety of advancing angles can be used, including those in the ranges from 100° to 170°; from 190° to 260°; and from 280° to 350°.

The scaffolds are stiff enough to render them self-supporting and to provide a biological cue for ovarian follicle development and also open enough to allow the ovarian follicles to grow and mature within the porous structure. By way of illustration, in some embodiments of the artificial ovaries, the scaffold has a shear modulus in the range from 50 Pa to 500 kPa, where the shear modulus is measured via oscillatory shear rheology at 30° C., as described in the Examples. This includes embodiments in which the scaffold has a shear modulus in the range from 500 Pa to 50 kPa, and further includes embodiments in which the scaffold has a shear modulus in the range from 1 kPa to 50 kPa, where the shear modulus is measured via oscillatory shear rheology at 30° C., as described in the Examples. where the shear modulus is measured via oscillatory shear rheology at 30° C., as described in the Examples.

The ink compositions used to print the three-dimensional scaffolds comprise water, the biocompatible polymer and, optionally, one or more types of ovarian somatic cells, bioactive factors, and/or additives, such as thickening agents, cross-linking agents, cross-linking initiators, and cell adhesion promoters and cell degradation promoters, such as cell adhesion or cell degradation peptide sequences. The amount of biocompatible polymer in the ink compositions will depend on the nature of the biocompatible polymer. The biocompatible polymer is typically a major (or majority) component in the ink compositions and the struts formed from the ink compositions. By way of illustration only, in some embodiments of the ink compositions the biocompatible polymer is present at concentrations in the range from about 0.5% to about 20% w/w. If bioactive factors and/or additives are present, they typically account for no greater than about 5% w/w of the ink compositions.

If ovarian cells and/or bioactive factors (discussed below) are present in the ink compositions, extrusion is desirably carried out at temperatures that are not greater than physiological temperatures. For example, extrusion may be carried out at temperature in the range from about 20° C. to about 40° C.

The biocompatible polymers in the ink compositions may include cross-linkable functionalities that allow them to be cross-linked prior to, during and/or after extrusion. The biocompatible polymers may cross-link directly or through cross-linking agents. Potential cross-linking chemistries that can be used include reactions between amines and carboxylic acids, acrylates and acrylates, acrylates and thiols, aldehydes and amines, and/or azides and alkynes.

Although the fabrication of a porous 3D scaffold is described in terms of 3D printing above, other techniques can be used to form the porous scaffolds from the compositions. For example the compositions can be freeze dried to form a foam or sponge-like scaffold or they can be cast into a porous micromold and then gelled.

For the purposes of this disclosure, a biocompatible polymer is a polymer that does not have a significant negative impact on cell viability or oocyte growth and viability and, for transplantable artificial ovaries, does not induce a negative reaction, such as a chronic immune response or inflammatory response in a patient into which it is implanted. Examples of biocompatible polymers include gelatin, collagen, fibrin, fibrinogen, alginate, polyethylene glycol, hyaluronic acid, peptides, heparin, laminin, fibronectin, or processed decellularized extracellular matrix, and combinations of two or more thereof. In some embodiments of the scaffolds, the biocompatible polymer comprises a processed decellularized ovarian extracellular matrix, such as a processed extracellular matrix from an ovarian cortex or an ovarian medulla. The extracellular matrices can be obtained from ovaries from which the endogenous cellular material has been removed using a decellularization solution, such as sodium dodecyl sulfate (SDS). The term "processed" is used here to indicate that the decellularized ovarian extracellular matrix is not used in its intact form, but rather is broken apart to some degree (for example, by slicing into thin sheets and/or subjecting it to enzymatic digestion) so that it's pieces can be used as a component in a non-naturally occurring (i.e., artificial), engineered ovary.

The struts of the scaffolds are can comprise or consist of biocompatible polymers that biogradable in vivo, such that the scaffold materials will ultimately biodegrade after implantation. This can be made possible by using nanoporous struts, such as hydrogel struts, in which allow biological tissue to grow around and/or through them, such that the in-grown tissue eventually replaces the artificial scaffold. For the purposes of this disclosure, a scaffold can be considered fully biodegradable if it completely degrades within 5 years of implantation in a patient. However, the scaffolds can be designed to biodegrade over much shorter periods, including periods of less than one year; periods of less than six months; and periods of less than one month.

The processed extracellular matrix can provide the only or substantially only biocompatible polymer in the scaffold, or it may be combined with one or more additional biocompatible polymers. For example, in some embodiments the extracellular matrix is sliced into pieces and those pieces are used to form the scaffold without additional polymers. In other embodiments, the extracellular matrix undergoes enzymatic digestion. A solution of the digested extracellular matrix, with or without other biocompatible polymers, can then be used to form the scaffold. In the latter embodiments, the extracellular matrix can be dried (e.g., lyophilized), cut into pieces and milled into a powder. The powder can then be enzymatically digested using, for example, a pepsin digestion that breaks down proteins and makes them soluble. A solution of the digested extracellular matrix and, optionally, other biocompatible polymers and/or bioactive factors, can then be printed, cast for freeze-drying or cast into a micromold to provide a porous scaffold. If the solution is cast into a micromold, the pH of the pepsin digest is desirably adjusted to physiological pH (e.g., 7.4) and the solution warmed (e.g., to 37° C.) to cause a gel to form. This gel can then be removed from mold. If the solution is printed, it can be gelled on a warm stage after printing or at least partially cross-linked prior to printing to make the solution into a printable gel. This can be accomplished using a polyethylene glycol crosslinker, as described in more detail below.

Some embodiments of the scaffolds comprise extrudable hydrogels formed via the gelation of the biocompatible polymer as the result of cross-linking. In these embodiments, the transition from solution to gel phase can render the hydrogels self-supporting. Self-supporting structures are characterized in that they substantially retain the 3D shape imparted to them by the extrusion process and do not require a supporting structure or matrix to maintain their shape and structural integrity. The use of hydrogels allows the scaffolds to comprise stiff matrices that are well-suited for biological cues, while still allowing the follicles to grow unimpeded. Gelatin hydrogels and poly(ethylene glycol) hydrogels, which comprise the biocompatible polymer cross-linked by poly(ethylene glycol) cross-linkers, are an example of a type of organic hydrogel that can be used to form the scaffolds in the artificial ovaries.

Bioactive factors that can be included in the scaffolds are substances that promote the growth of ovarian cells in the scaffold. Examples of bioactive factors include genes, proteins, peptides, growth factors, pharmaceutical compounds, hormones, steroids, antibiotics and the like. Although the bioactive factors may be polymers (e.g., proteins and peptides), they are a distinct component from the biocompatible polymer and they do not provide a continuous matrix in the porous scaffolds. Rather than, or in addition to, being added to the ink compositions, the bioactive factors can be applied to the scaffolds after the scaffolds have been constructed.

A wide variety of artificial ovary designs are possible, including those in which different materials and/or cells are printed, seeded onto, and/or coated onto different portions of the scaffold. In addition, the printing process can be controlled such that the average pore diameter differs in different portions of the scaffold. The following embodiments are provided for illustration.

One embodiment of an artificial ovary comprises a scaffold comprising an organic hydrogel coated with processed natural ovarian extracellular matrix by infusing the hydrogel with a solution of the processed extracellular matrix (created from pepsin digest) and either allowing the solution to dry or causing gelation of the matrix by warming to 37° C.

Another embodiment of an artificial ovary comprises a multilayered (e.g., a bilayered) scaffold printed from layers comprising processed ovarian cortex extracellular matrix and subsequently those comprising processed ovarian medulla extracellular matrix in order to simulate the outer and inner portions of a natural ovary. This artificial ovary could comprise an ovarian medulla mimicking region in which the struts comprise processed ovarian medulla extracellular matrix and an ovarian cortex mimicking region in which the struts comprise processed ovarian cortex extracellular matrix. In some embodiments of the artificial ovary, the ovarian medulla mimicking region has a lower shear modulus than the ovarian cortex mimicking region. For example the ovarian medulla mimicking region can have a shear modulus in the range from 1000 Pa to 10 kPa (G') (e.g., from 1000 Pa to 5 kPa) and the ovarian cortex mimicking region can have a shear modulus in the range from 10 kPa to 100 kPa (G') (e.g. from 20 kPa to 100 kPa). This is of interest because follicles of specific stages of their growth can be found in these areas and they have different stiffnesses. The cortex and medulla also contain different biochemical cues that may influence the follicles and cells differently. The relative stiffness of the different regions can be achieved, for example, by using different biocompatible polymers; different concentrations of the same biocompatible polymers; different cross-linking agents; and/or different crosslinking densities. By way of illustration only, the ovarian follicles can be concentrated in the cortex mimicking region of the scaffold and the struts in the medulla mimicking regions can comprise stroma cells and endothelial cells that enable vascularization of the scaffold.

Another embodiment of an artificial ovary comprises a follicle-seeded scaffold in which follicles of different developmental stages are concentrated in different, spatially distinct, regions of the scaffold, where a type of follicle is considered concentrated in a given region if that region has a higher concentration of that follicle type than of any other follicle type. For example, primordial follicles can be concentrated in a first region of the scaffold, primary follicles can be concentrated in a second region of the scaffold, secondary follicles can be concentrated in a third region of the scaffold, and/or antral follicles can be concentrated in a fourth region of the scaffold. The different regions may be directly adjacent, or may be spatially separated by distances ranging, for example, from 10 µm to 1 cm. In these embodiments, the different types of follicles can be completely isolated within their distinct regions. However, it is also possible for the regions to overlap at their edges. Optionally, the pores within each of the different regions can be tailored to the developmental stage of the follicles to be seeded therein. For example, the average pore size in the first region can be smaller than the average pore size in the second region, the average pore size in the second region can be smaller than the average pore size in the third region, and the average pore size in the third region can be smaller than the average pore size in the fourth region. By way of illustration, one region may be printed with an average pore size of less than 400 µm (e.g., from 50 to 300 µm), another region may be printed with an average pore size in the range from 400 to 600 µm, and another region may be printed with an average pore size of greater than 600 µm (e.g. in the range from 800 µm to 2000 µm).

Yet another embodiment of an artificial ovary comprises a scaffold comprising an organic hydrogel into which ovarian stroma cells are incorporated by including the stroma cells in the ink composition used to print the scaffold. In still another embodiment, an artificial ovary comprises endothelial cells seeded onto a scaffold by depositing a concentrated cell solution onto a scaffold in order to provide a pre-vascularized artificial ovary.

Once the scaffolds are formed and seeded with ovarian follicles and, optionally, other biological cells, they can be cultured in an appropriate culture medium in vitro or implanted into a living subject to promote follicle growth and development and even oocyte ovulation.

The artificial ovaries can be used to mature and then ovulate one or more viable oocytes in vitro, which can then be implanted into a patient in an IVF procedure. This can be done by culturing the artificial ovary in the presence of an ovulation-inducing hormone at a physiological temperature for a time sufficient for at least one oocyte in at least one ovarian follicle to mature to metaphase II, wherein the viable metaphase II oocyte is expelled from the follicle via cumulus cell expansion and out of the artificial ovary. Prior to the exposure to the ovulation-inducing hormone, the follicles can be matured to a desired stage or size in the absence of the hormone. Ovulation-inducing hormones include luteinizing hormone (LH) or a functionally equivalent ligand, such as chorionic gonadotropin.

Alternatively, the artificial ovaries can be implanted in vivo to improve or restore fertility and/or to improve or restore ovarian endocrine function to a mammalian patient from which at least a portion of a natural ovary has been removed from its native site. This is accomplished by implanting the artificial ovary in vivo at the native site at which at least a portion of the natural ovary was removed, whereby one or more of the ovarian follicles are capable of ovulating a viable oocyte in vivo post-implantation. The ovulation of one of more oocytes is induced naturally in the in vivo environment post-implantation and the ovulated oocytes can then be fertilized naturally and produce a live birth. Even in the absence of ovulation, the patient's natural ovarian function can be improved because the implanted artificial ovary can at least partially restore ovarian endocrine function. The native site can be, for example, an ovarian bursa from which the ovary has been removed. Prior to the implantation, the artificial ovary can be cultured in a growth medium until the follicles have matured to a desired stage or size.

EXAMPLES

Example 1

This example illustrates the fabrication and functioning of an artificial ovary.

Methods and Materials:

A 10% (w/v) gelatin solution in phosphate-buffered saline solution (PBS) was prepared at 37° C. The solution was loaded into a printing cartridge while a liquid and subsequently, the cartridge was cooled to 32° C. and fixed with a 100 µm stainless steel tip. Scaffolds were printed onto glass slides using the EnvisionTEC 3D-Bioplotter. Scaffolds in the shape of 8×8 mm rectangles with thicknesses of ~500-750 µm were printed at extruding pressures and speed of 4.5-5.0 bar and 10 mm/s, respectively. Layers advanced at either 90° or 60° and the printed strands (fibers) were separated by a distance of 600 µm. The printing and material parameters were optimized to print well-defined gelatin scaffolds resulting in either a grid-like pattern (FIG. 1A) or a tortuous pore network (FIG. 1B)

The scaffolds were cross-linked in an aqueous solution of 15 mM EDC and 6 mM NHS for 1.5 hours. The EDC/NHS cross-linking and scaffold architecture was assessed by light microscopy. The scaffolds were then washed with phosphate buffered saline (PBS) and lyophilized on a tray lyophilizer and stored in a desiccator until use.

The scaffolds were rehydrated in PBS and cut into 4 mm cylinders with a biopsy punch. The scaffolds were then submerged in 70% ethanol and exposed to UV light for sterilization. Scaffolds were washed with PBS and stored in PBS overnight in the refrigerator prior to seeding.

Murine ovarian somatic cells were isolated by plating ovarian enzymatic digestion with collagenase to select for adherent cells. Scaffolds were seeded with ovarian stroma cells at seeding densities ranging from 0 to 444,000 cells per scaffold. Each scaffold was seeded with 4 µL of the concentrated cell suspension after trypsinizing the cells. Optionally, somatic cells were seeded onto scaffolds one day prior to follicle seeding.

Murine follicles were mechanically and enzymatically isolated from excised ovaries. Secondary follicles (150-200 µm diameter) were selected and seeded into the pores of the gelatin scaffolds by mouth pipetting and cultured up to 8 days. Cell viability and arrangement were analyzed by confocal fluorescence microscopy using Live/Dead and CellTracker stains. Oocyte diameter was monitored by light microscopy and estradiol content of media was assessed by ELISA.

Results: The resulting 3D printed gelatin scaffolds provided adhesion of somatic cells on the struts as well as sufficient space for follicles to infiltrate and reside within the scaffold pores (FIG. 1C). Somatic cells also started to surround follicles over time (FIG. 1C inset). Although follicles are difficult to culture longer term, these follicles remained viable within the 3D printed gelatin scaffolds for 8 days. Furthermore, follicles (oocytes) displayed growth in the scaffolds, and somatic cells demonstrated normal function, continually producing estradiol over the culture period (FIG. 1D, H). When pore geometries were compared, follicles made more intimate contacts with the scaffold in the tortuous pattern over the grid pattern (FIG. 1E). Follicles with only 1 scaffold contact resulted in a 50% survival rate, but with 2 or more resulted in 82.8% survival. This was evident when follicles maintained spheroid-shape in scaffold pore corners, but dissociated when scaffold contact was limited (FIG. 1E-G).

Conclusions: This example demonstrates well-defined 3D printed scaffolds as an artificial environment for supporting follicle health and growth. We leveraged the advantages of 3D printing to understand the important effects of scaffold geometry on the behavior of follicles in vitro.

Example 2

This example illustrates the use of an artificial ovary to restore ovarian endocrine function; ovulate a viable egg; and restore fertility in a mammalian patient.

3D Ink Preparation and 3D Printing:

1 g of gelatin (porcine, type A, Sigma Aldrich)) was dissolved in 10 mL of phosphate-buffered saline solution (PBS) (pH=7.4) at 37° C. The solution was subsequently loaded in a stainless steel printing cartridge and an agarose piston was placed on top of the solution. The cartridge was then maintained at 30° C. for at least 3 hours to cool the solution into a gel. With an EnvisionTEC 3D-Bioplotter, gelatin was printed from a 100 µm stainless steel nozzle onto glass slides maintained at 10° C. Extruding pressures ranged from 1.8 to 3.2 bar to control ink flow rates, and the ink was printed at a speed to 10 mm/s into 15×15 mm squares, 5 layers thick. The first layer was completely solid (no spacing between struts) whereas the distance between struts (from middle of one strut to middle of adjacent strut) on all subsequent layers was 600 µm. Three types of microporous internal architectures were printed with advancing angles between layers of 30°, 60°, and 90°. An image of the scaffold printed at an advancing angle of 60° is shown in FIG. 2A.

Scaffold Preparation:

After printing, structures were kept in a closed, humid container and on ice. Structures were cross-linked for 1 hour with a 15 mM N-(3-Dimethylaminopropyl)-N'-ethylcarbodiimide (EDC) (Sigma Aldrich)/6 mM N-hydroxysuccinimide (NETS) (Sigma Aldrich) solution in deionized water to stabilize gelatin scaffolds at physiological temperature. Scaffolds were then washed with deionized water, and sterilized by overnight incubation in 70% ethanol as well as 1 hour of UV exposure. Scaffolds were then stored in sterile PBS at 4° C. Prior to culture, scaffolds were biopsy punched into 2, 3, or 4 mm diameter cylinders and transferred to transwells.

Ink and Scaffold Characterization:

Oscillatory shear rheology was performed with the gelatin on an Anton-Paar MCR 302 rheometer. Rheology was conducted with a cone (2°)-plate fixture and at 10 rad/s. Temperature of the stage was controlled between 15° C. and 40° C. via a Peltier system. Gelatin was loaded onto the stage while warm (37° C.) and after lowering the cone fixture into position, the edges were covered with mineral oil to prevent dehydration. Temperature sweep was conducted at 0.5° C./min and at 1% strain.

The results of the shear rheology measurements are shown in FIGS. 2B and 2C. FIG. 2B shows the gelation profile of the gelatin over 40 to 15° C. FIG. 2C shows the response of 30° C. gelatin to increasing strains. The point of catastrophic failure (518% strain) characterizes the ink's printability.

The architecture of scaffolds was analyzed from photographs and images taken with a Photojojo macrolens and cell phone camera along with a Leica M205 C stereoscope. For 3D imaging, scaffolds were fluorescently labeled with NHS-rhodamine (Thermo-Scientific) and were dialyzed against PBS. NHS-rhodamine was dissolved in dimethyl sulfoxide (DMSO) at 10 mg/mL. A 100× diluted solution of the concentrate in PBS was used for labeling for 1-2 hours. Labeled scaffolds were then imaged a Nikon A1R laser scanning confocal microscope.

Follicle-Scaffold Interaction 3D Analysis:

EGFP-expressing follicles were seeded into NHS-rhodamine labeled scaffolds and cultured. Two scaffolds per geometry (30°/60°/90°) with four follicles each were analyzed. After 2 days, the follicles were analyzed by confocal fluorescence microscopy at an image slice thickness of 5.3 µm. Images were analyzed as image stacks as well as 3D reconstructions in NIS Elements software. To quantify the number of follicle contacts with the scaffold, the image was scrolled through to identify slices where the follicle was flush with the scaffold. Side contacts were then quantified by scrolling the slices to find the longest length of contact (the longest area of green fluorescent cells along a strut) and measuring. Bottom scaffold contacts were determined if red fluorescence was observed underneath of green fluorescence within 20 µm. Images were compared to light microscopy images and follicles that had moved from transferring for imaging where eliminated. Some side length contacts could not be quantified due to air bubbles.

Figure 3J:
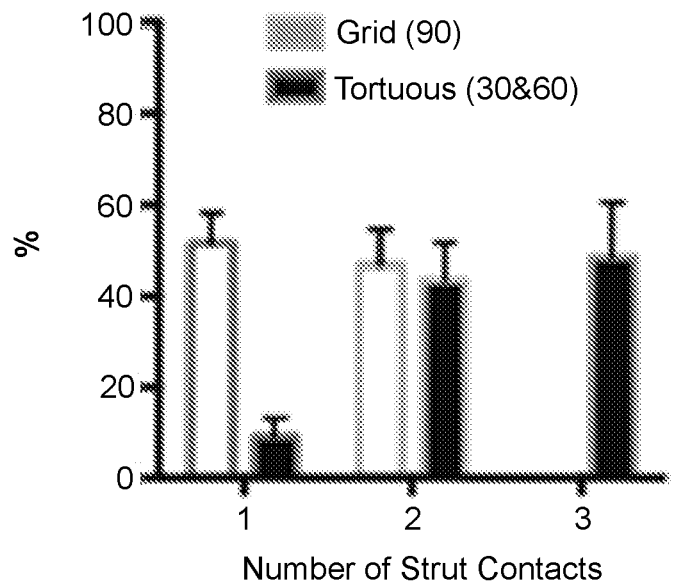
FIG. 3J is a graph showing the percent of follicles having one, two, or three strut contacts for scaffolds printed at advancing angles of 30°, 60°, and 90°.

The 3D reconstructions are shown in FIGS. 3A-3J. FIGS. 3A, 3B, and 3C show the 3D reconstructions of the confocal fluorescence images of stack layers comprising struts printed at advancing angles of 30°, 60°, and 90°, respectively. FIGS. 3D, 3E, and 3F show the 3D reconstructions of the corresponding pores in the confocal fluorescence images of the stacked layers comprising struts printed at advancing angles of 30°, 60°, and 90°, respectively. The shading corresponds to depth of pore according to a heat map. FIGS. 3G, 3H, and 3I show the corresponding EGFP-expressing follicles seeded in the pores, after 2 days. Follicles in pores in the scaffolds printed at 30° and 60° advancing angles tended to reside in corners, whereas follicles in pores in the scaffolds printed at 90° were more likely to be along only one strut.

Figure 3K:
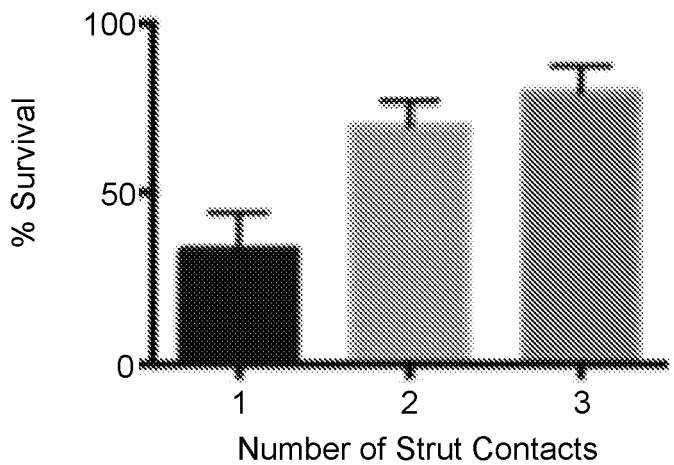
FIG. 3K is a graph of the follicle survival as a function of the number of strut contacts.
Figure 3L:
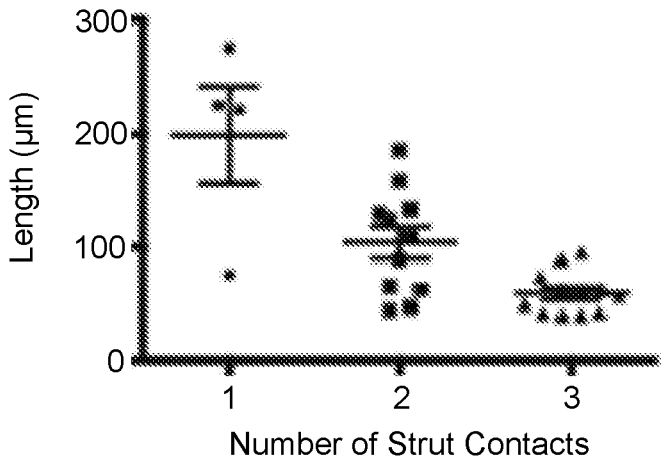
FIG. 3L is a graph of the follicle length of the follicle-strut adhesion area as a function of the number of strut contacts.

FIG. 3J is a graph showing the percent of follicles having one, two, or three strut contacts for scaffolds printed at advancing angles of 30°, 60°, and 90°. FIGS. 3K and 3L are graphs of the follicle survival and the length of the follicle-strut adhesion area, respectively, as a function of the number of strut contacts. As shown in these graphs, when seeded into scaffolds having advancing angles of 30° and 60°, follicles were most likely to have two or three scaffold contacts, whereas follicles in scaffolds having an advancing angle of 90° had an equal chance of making only one contact. In addition, follicle survival increased with the number of scaffold contacts and, as the number of strut contacts increased, the length of follicle adhesion along one strut decreased.

Immunofluorescence of Follicles with Scaffolds:

Immunofluorescence staining was conducted as described by Suri et al. (Shalu Suri, Christine E. Schmidt. "Cell-Laden Hydrogel Constructs of Hyaluronic Acid, Collagen and Laminin for Neural Tissue Engineering." *Tissue Engineering: Part A*. 16 (5). (2010).) Briefly, constructs were fixed for 40 minutes with chilled 4% paraformaldehyde and then washed with chilled PBS. Constructs were blocked and permeabilized with chilled 0.3% Triton X-100+10% FBS in PBS for 45 minutes. Primary antibodies in the previously described blocking solution were incubated either for 6 hours or overnight. After washing with PBS, the secondary antibody was labeled for 2 to 6 hours, followed by PBS washing and counterstaining with DAPI.

Follicle Isolation, Seeding, Culture and in Vitro Ovulation (& Survival):

Scaffolds were prepared by using a 2 mm or 3 mm biopsy punch onto the printed design and using a scalpel to lift each piece off of the slide. A thin spatula or flat forceps were used to place the scaffold punches on 0.4µ pore 12 mm transwells [Millipore] in a 24 well plate. Each well was filled with 400 µl of growth media (50% αMEM Glutamax and 50% F-12 Glutamax supplemented with 3 mg/ml bovine serum albumin (BSA, Sigma-Aldrich), 10 mIU/ml recombinant follicle-stimulating hormone (rFSH; from A. F. Parlow, National Hormone and Peptide Program, National Institute of Diabetes and Digestive and Kidney Diseases, Bethesda, Md., USA), 1 mg/ml bovine fetuin (Sigma-Aldrich), 5 µg/ml insulin, 5 µg/ml transferrin, and 5 µg/ml selenium (Sigma-Aldrich).

Multilayer secondary follicles (150-180 µm) were isolated from 16-day-old CD-1 female mice as previously described and under a Northwestern University Animal Care and Use Committee-approved protocol. (Xu, M., West, E., Shea, L. D. & Woodruff, T. K. Identification of a Stage-Specific Permissive In Vitro Culture Environment for Follicle Growth and Oocyte Development. *Biology of Reproduction* 75, 916-923 (2006).) Briefly, ovaries were removed from the bursas and were mechanically isolated with insulin needles in a glass dish containing dissociation media made of Leibovitz's L-15 Medium (Gibco) with 0.5% Penicillin-Streptomycin (Gibco) and 10% fetal bovine serum (FBS, Gibco). Only follicles that displayed intact morphology were selected for seeding and culture. Follicles were seeded by mouth-pipetting onto scaffolds and removing excess fluid from the top of the transwell. Follicles on scaffolds were cultured at 37° C. in 5% $CO_2$ in air for up to 8 days. Half of the growth media (200 µl) was replaced every other day. Spent media was stored at −20° C. and analyzed for estradiol (below). Follicles were imaged after seeding and at each media change using a Nikon dissecting scope. Follicles were scored as alive if the oocyte was visible, round and generally centralized through light microscopy.

Figure 4C:
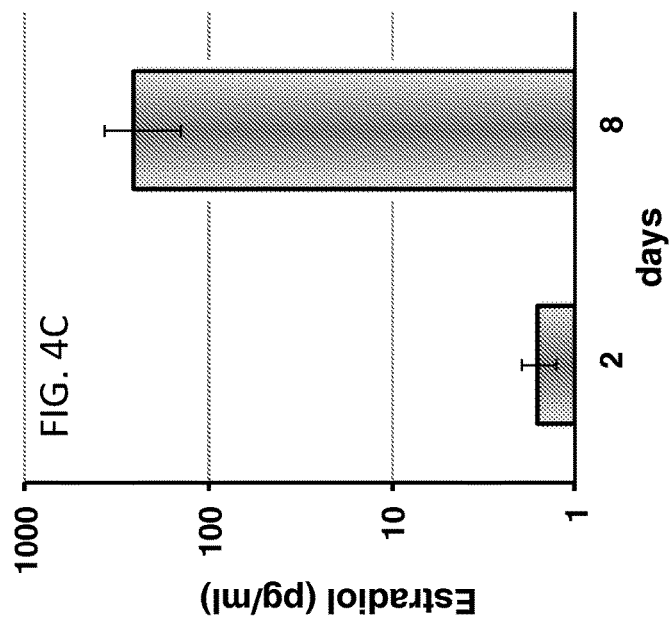
FIG. 4C is a graph of the concentration of estradiol detected in the media of follicles cultured within 30° or 60° scaffolds.
Figure 4A:
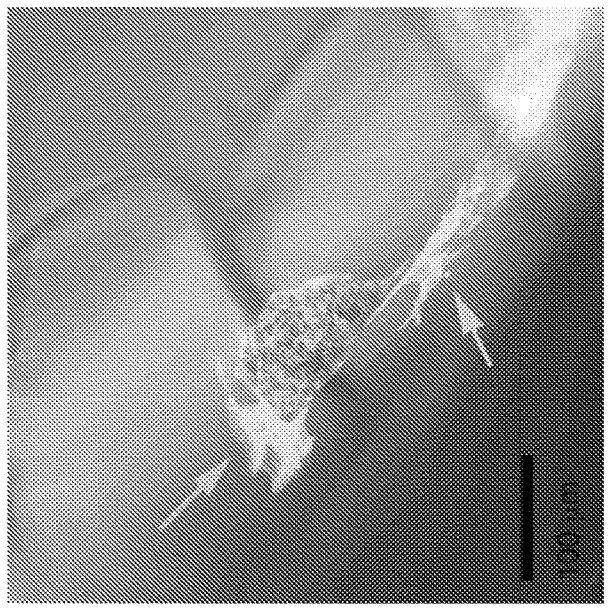
FIG. 4A is a confocal microscope fluorescent image overlayed with brightfield image that revealed clear gelatin struts and seeded secondary follicles.

FIG. 4A is a confocal microscope fluorescent image overlayed with brightfield image that revealed clear gelatin struts. By day 2 of culture, the cells along the periphery of the follicle robustly expressed vinculin, a cell adhesion molecule, along the gelatin struts (DNA).

In vitro ovulation was performed on 6-8 days of follicle culture or when the oocytes grew to about 70 µm. Follicles incubated for 16 h at 37° C. in 5% $CO_2$ in air in maturation media (αMEM with 10% fetal bovine serum, 1.5 IU/ml human chorionic gonadotropin (hCG), 10 ng/ml epidermal growth factor (EGF, BD Biosciences, Franklin Lakes, N.J., USA), and 10 mIU/ml rFSH). Oocytes were classified as metaphase II (MII). Gametes obtained following oocyte maturation were fixed in 3.8% paraformaldehyde containing 0.1% Triton X-100 (Sigma-Aldrich, St. Louis, Mo., USA) for 1 h at 37° C. for spindle morphology and chromosome alignment analysis. Oocytes were washed 3 times in blocking solution with 1×PBS containing 0.3% BSA and 0.01% Tween-20, incubated overnight in a 1:50 dilution of mouse anti-α-tubulin (Cell Signaling Technology, Danvers, Mass., USA) in blocking solution. Then, oocytes were washed 3 times with blocking solution, mounted using Vectashield containing DAPI (Vector Laboratories, Burlingame, Calif., USA), and analyzed using an EVOS FL AUTO microscope (Life Technology, Grand Island, N.Y., USA). Oocytes with barrel-shaped bipolar spindles and well-organized microtubule fibers, along with tightly aligned chromosomes on the metaphase plate, were scored as normal (Xiao, S. et al. Size-specific follicle selection improves mouse oocyte reproductive outcomes. *Reproduction* (2015). doi:10.1530/REP-15-0175.)

3βHSD Staining and H&E Staining:

To verify the presence of an intact theca cell layer, follicles within the scaffolds were rinsed with PBS then stained with 3b-hydroxysteroid dehydrogenase (3βHSD) solution containing 0.12 mg/mL nitroblue tetrazolium chloride, 0.25 mg/mL beta-nicotinamide adenine dinucleotide hydrate (b-NADþ), and 0.025 mg/mL epiandrosterone (Sigma-Aldrich) in PBS for up to 3 hours at room temperature wrapped in foil (Krummer, 1994). Negative controls were performed on follicles for the same length of time in solution without b-NADþ and in PBS alone. Cells were considered positive of 3βHSD if they were purplish brown in color and the negative controls were not positive for this color change.

Follicles on scaffolds were fixed with 4% PFA. The scaffolds were embedded in calcium-alginate and dehydrated in 50%, 60% and 70%. All tissue processing and hematoxylin and eosin (H&E) staining was performed by the Northwestern University Center for Reproductive Sciences Histology Core. Fixed tissue was processed using an automated tissue processor (Leica) and embedded in paraffin. Serial sections were cut 5 mm thick and selected slides were stained with hematoxylin and eosin using a Leica Autostainer XL (Leica Microsystems).

Figure 4B:
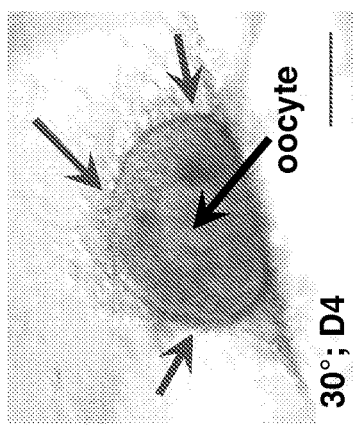
FIG. 4B shows the 3βHSD stain performed on live follicles seeded into a scaffolds with a 30° advancing angle cultured for 4 days.
Figure 4E:
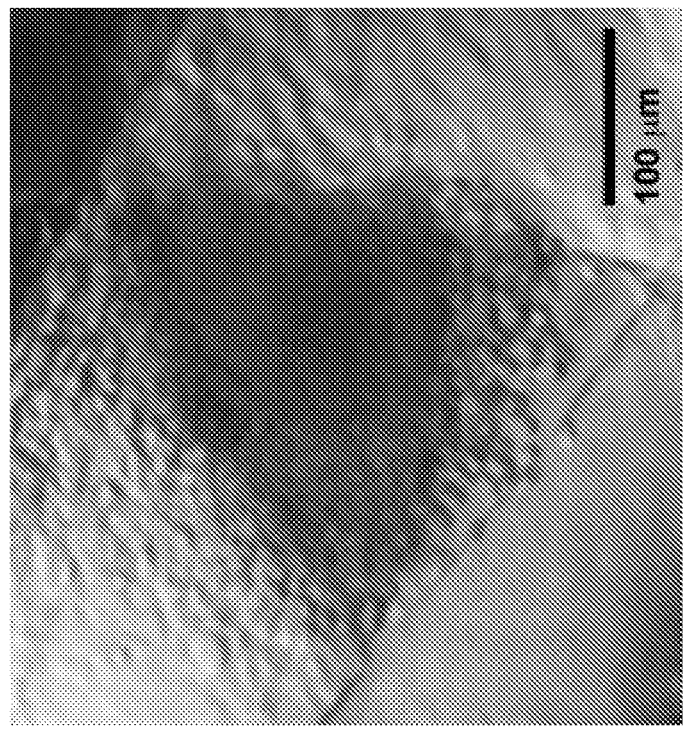
FIG. 4E is an image of cumulus cell expansion observed following incubation in maturation medium containing hCG for 16 hours.
Figure 4D:
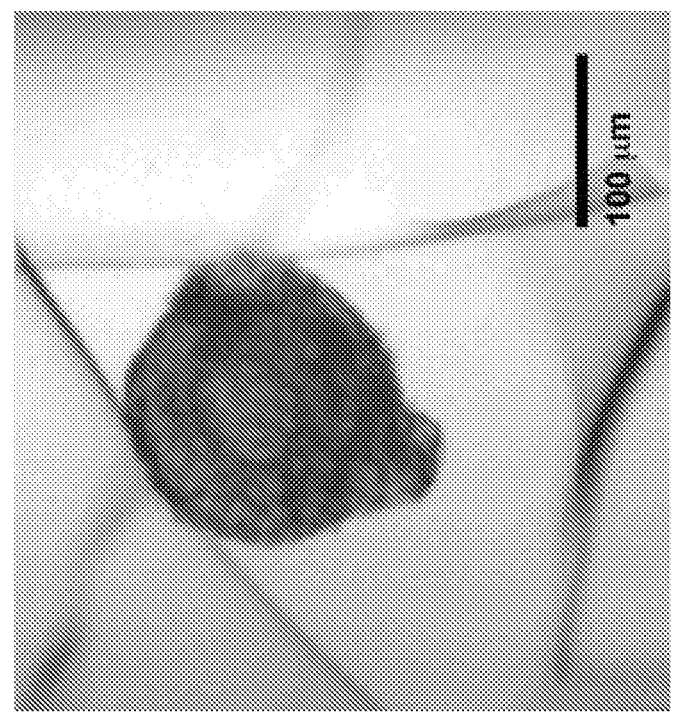
FIG. 4D is an image of follicles seeded into the struts of 60° scaffolds visualized by light microscopy on day 1 and cultured for 7 days.
Figure 4G:
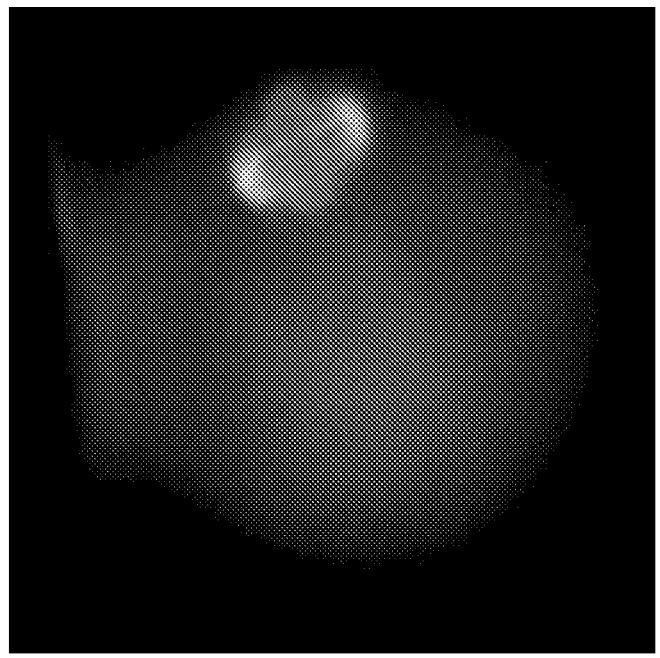
FIG. 4G is a confocal fluorescent microscope image used to identify normal chromosome alignment and spindle morphology of an MII egg.
Figure 4F:
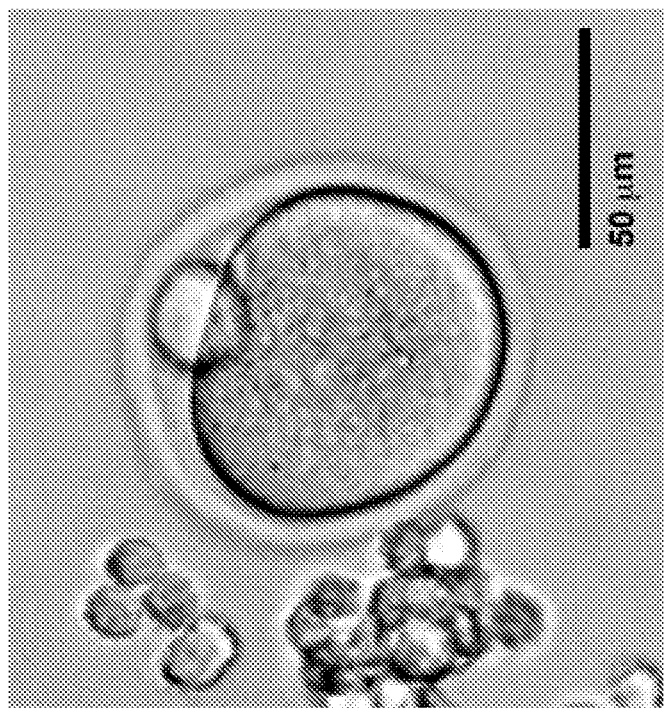
FIG. 4F is an image of an MII egg with polar body extrusion that had ovulated through the scaffold pores.

FIG. 4B shows the 3βHSD stain performed on live follicles seeded into the scaffolds with a 30° advancing angle cultured for 4 days. Light microscopy revealed purple stained squamous cells (lighter arrows) along the periphery of the follicle, indicative of Theca cells aromatase activity. FIG. 4C is a graph of the concentration of estradiol detected in the media of follicles cultured within 30° or 60° scaffolds, showing an increase over time from an average of 1.6 pg/ml at day 2 to 255 pg/ml at day 8. FIG. 4D is an image of follicles seeded into the struts of 60° scaffolds visualized by light microscopy on day 1 and cultured for 7 days. FIG. 4E is an image of cumulus cell expansion observed following incubation in maturation medium containing hCG for 16 hours. FIG. 4F is an image of an MII egg with polar body extrusion that had ovulated through the scaffold pores. FIG. 4G is a confocal fluorescent microscope image was used to identify normal MII spindle morphology and chromosome alignment.

Estradiol ELISA:

Terminal blood draws were processed to collect serum. Serum and media estradiol was detected using an ELISa kit (Elisa; Calbiotech, ES180S) and serum inhibin A (Ansh, AL-123) were tested. Both sets of data are analyzed using GraphPads Prism software.

Intrabursal Surgeries, Mating, Vaginal Smear:

Mice ubiquitously expressing the enhanced green fluorescent protein (eGFP, Jackson Labs) were used to create the ovary prostheses and were identified using a BlueStar light with VG1 filter glasses (EMS). 2 mm scaffolds were prepared as described above on transwells and with growth medium. Primordial, primary, and secondary follicles from eGFP+ females were seeded as described above over two days, seeding small follicles on the bottom solid layer of the scaffold and filling in the remaining scaffold on the second day with mostly larger follicles up to multilayered secondary follicles. These scaffolds were cultured for 4 days prior to surgeries and imaged on the morning before the surgeries. Sham transplant scaffolds were prepared the same way, but did not include cells.

Animal use was performed under a Northwestern University Animal Care and Use Committee-approved protocol. Intrabursal surgeries were performed on 8-10 week old NSG females (Jackson Labs). Mice were anesthetized with a mixture of 100 mg/kg of ketamine and 15 mg/kg of xylazine. The upper uterine horn, oviduct and ovarian bursa was visualized and brought out of the body cavity to perform the surgery. The ovarian artery was located and flow was inhibited with a 10 gauge suture tie. The ovary was removed completely while maintaining the integrity of the bursa and bursal cavity. The ovary bioprosthesis was inserted into the ovarian bursa, cell side toward the oviducts and enclosed within the bursa by 1 or 2 stitches with 10 gauge nylon sutures. This was repeated for both ovaries. Shame surgeries were performed like these surgeries but with scaffolds that did not contain any cells. 7 mice with ovary bioprostheses and 2 mice with sham surgeries were mated with CD1 males that had previously sired pups. 1 female was paired with 1 male 4 days after surgery and housed together for 25 days or more. The presence of a solid plug within the mated female vagina indicated a successful mating.

Vaginal cytology was analyzed on pre and post surgical mice daily between 09:00 and 10:00. Approximately 150 µl of filtered saline was used for vaginal lavage and pipetted into a 48-well plate. The collected cells were imaged on a Leica DM600 inverted microscope. Stages of the estrous cycle were classified according to the vaginal cell morphology (Nelson, J. F., Felicio, L. S., Randall, P. K., Sims, C. & Finch, C. E. A longitudinal study of estrous cyclicity in aging C57BL/6J mice: I. Cycle frequency, length and vaginal cytology. *Biology of Reproduction* 27, 327-339 (1982).)

A transplant recipient with naturally born pup was imaged through filter lenses and under BlueStar flash light to reveal a eGFP+ pup and a eGFP- mom. The mom had prominent nipples whereas the nipples of the transplant recipient that had not given birth had less prominent nipples. Milk within the belly of 4-day old pup indicated a lactating and nursing mom.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An artificial ovary comprising:
   a porous three-dimensional scaffold comprising a plurality of overlapping struts, the struts comprising a biocompatible polymer and defining a network of pores; and
   a plurality of ovarian follicles disposed inside the pores;
   wherein the artificial ovary is capable of supporting at least one of: an ovarian endocrine function; or ovulation of one or more mature oocytes from one or more of the ovarian follicles, when the artificial ovary is cultured in vitro or implanted in a mammalian subject in vivo,
   provided that if the biocompatible polymer comprises ovarian extracellular matrix, then that ovarian extracellular matrix comprises processed decellularized ovarian extracellular matrix.

2. The artificial ovary of claim 1, capable of ovulating one or more mature oocytes from one or more of the ovarian follicles when cultured in the presence of an ovulation-inducing hormone.

3. The artificial ovary of claim 1, capable of ovulating one or more mature oocytes from one or more of the ovarian follicles when implanted in a mammalian subject in vivo.

4. The artificial ovary of claim 1, wherein the struts have a substantially regular cross-section along their lengths.

5. The artificial ovary of claim 1, wherein the struts have an average cross-sectional diameter in the range of 10 µm to 1 mm.

6. The artificial ovary of claim 5, wherein the struts are substantially aligned and the spacing between the substantially aligned struts is in the range from 50 µm to 1 mm.

7. The artificial ovary of claim 4, wherein the cross-sectional diameters of the struts vary by no more than ±20% along their lengths.

8. The artificial ovary of claim 4, wherein the struts are arranged in adjacent stacked layers, each layer comprising a plurality of substantially aligned struts, and the substantially aligned struts in adjacent layers define advancing angles that are in the range from 0° to 360°.

9. The artificial ovary of claim 8, wherein the pores are sized such that, on average, the ovarian follicles inside the pores contact at least two of the struts.

10. The artificial ovary of claim 9, wherein the struts have an average cross-sectional diameter in the range of 10 µm to 1 mm.

11. The artificial ovary of claim 9, wherein the advancing angles are in the range from 20° to 80°.

12. The artificial ovary of claim 9, wherein the struts are biodegradable;
the biocompatible polymer comprises a gelatin hydrogel;
the advancing angles are in the range from 25° to 75°;
and the spacing between the substantially aligned struts is in the range from 100 μm to 500 μm.

13. The artificial ovary of claim 11, wherein the spacing between the substantially aligned struts is in the range from 50 μm to 1 mm.

14. The artificial ovary of claim 1, wherein the struts are biodegradable.

15. The artificial ovary of claim 14, characterized in that the porous three-dimensional scaffold completely degrades within five years in vivo in a mammalian subject.

16. The artificial ovary of claim 14, characterized in that the porous three-dimensional scaffold completely degrades within five years in vivo in a human subject.

17. The artificial ovary of claim 14, wherein the biocompatible polymer is a gelatin hydrogel.

18. The artificial ovary of claim 17, wherein the struts consist of a gelatin hydrogel.

19. The artificial ovary of claim 1, wherein the biocompatible polymer is processed decellularized extracellular matrix.

20. The artificial ovary of claim 1, wherein the biocompatible polymer comprises a poly(ethylene glycol) hydrogel.

21. The artificial ovary of claim 1, wherein the biocompatible polymer comprises enzymatically digested decellularized ovarian extracellular matrix.

22. The artificial ovary of claim 1, wherein the biocompatible polymer comprises decellularized ovarian extracellular matrix that has been sliced into pieces.

23. The artificial ovary of claim 1, wherein the biocompatible polymer comprises a decellularized ovarian extracellular matrix powder.

24. The artificial ovary of claim 1, further comprising ovarian somatic cells incorporated into or adhered onto the struts, wherein the ovarian somatic cells comprise ovarian stroma cells, endothelial cells, pericytes, pericyte precursor cells, or a combination of two or more thereof.

25. The artificial ovary of claim 1, wherein the plurality of ovarian follicles comprises at least two types of ovarian follicles in different developmental stages selected from primordial ovarian follicles, primary ovarian follicles, secondary ovarian follicles, and antral ovarian follicles.

26. The artificial ovary of claim 25, wherein the first of the at least two types of ovarian follicles are concentrated in a first region of the scaffold and the second of the at least two types of ovarian follicles are concentrated in a second region of the scaffold that is spatially distinct from the first region of the scaffold.

27. The artificial ovary of claim 26, wherein the average size of the first type of ovarian follicle is smaller than the average size of the second type of ovarian follicle, and the average pore size in the first region of the scaffold is smaller than the average pore size in the second region of the scaffold.

28. The artificial ovary of claim 27, wherein the scaffold comprises an ovarian medulla mimicking region and an ovarian cortex mimicking region, and the ovarian medulla mimicking region has a lower shear modulus than the ovarian cortex mimicking region.

29. The artificial ovary of claim 25, wherein the plurality of ovarian follicles comprises at least three types of ovarian follicles in different developmental stages selected from primordial ovarian follicles, primary ovarian follicles, secondary ovarian follicles, and antral ovarian follicles.

30. The artificial ovary of claim 1, wherein the scaffold comprises an ovarian medulla mimicking region in which the struts comprise processed ovarian medulla extracellular matrix and an ovarian cortex mimicking region in which the struts comprise processed ovarian cortex extracellular matrix.

31. The artificial ovary of claim 30, wherein the scaffold comprises an ovarian medulla mimicking region and an ovarian cortex mimicking region, and the ovarian medulla mimicking region has a lower shear modulus than the ovarian cortex mimicking region.

32. The artificial ovary of claim 1, wherein the scaffold comprises an ovarian medulla mimicking region and an ovarian cortex mimicking region, and the ovarian medulla mimicking region has a lower shear modulus than the ovarian cortex mimicking region.

33. A method of ovulating a viable oocyte in vitro using the artificial ovary of claim 1, the method comprising: culturing the artificial ovary in the presence of an ovulation-inducing hormone at a physiological temperature for a time sufficient for at least one oocyte in at least one ovarian follicle to mature to metaphase II, wherein the viable metaphase II oocyte is expelled from the follicle via cumulus cell expansion.

34. A method improving or restoring fertility to a mammalian patient from which at least a portion of a natural ovary has been removed from its native site, the method comprising implanting the artificial ovary of claim 1 in vivo at the native site, whereby one or more of the ovarian follicles are capable of ovulating a viable oocyte in vivo post-implantation.

35. A method of improving or restoring ovarian function to a mammalian patient from which at least a portion of a natural ovary has been removed from its native site, the method comprising implanting the artificial ovary of claim 1 in vivo at the native site, whereby ovarian endocrine function of the patient is improved post-implantation.

* * * * *

UNITED STATES PATENT AND TRADEMARK OFFICE
CERTIFICATE OF CORRECTION

PATENT NO. : 10,479,980 B2
APPLICATION NO. : 15/545175
DATED : November 19, 2019
INVENTOR(S) : Monica M. Laronda et al.

Page 1 of 1

It is certified that error appears in the above-identified patent and that said Letters Patent is hereby corrected as shown below:

In the Specification

Column 1, Lines 16-19:
Delete the phrase:
"This invention was made with government support under K01 DK099454 and HD079188 awarded by the National Institutes of Health. The government has certain rights in the invention."
And replace with:
--This invention was made with government support under K01 DK099454 and HD076188 awarded by the National Institutes of Health. The government has certain rights in the invention.--.

Signed and Sealed this
Second Day of August, 2022

Katherine Kelly Vidal
*Director of the United States Patent and Trademark Office*